United States Patent [19]

Ohno et al.

[11] Patent Number: 4,997,972
[45] Date of Patent: Mar. 5, 1991

[54] 2-ACYLAMINO-5-HALOGENATED-CINNAMIC ACID DERIVATIVE AND METHOD FOR ITS PRODUCTION

[75] Inventors: Hiroaki Ohno; Daisaku Matsunaga, both of Tokyo, Japan

[73] Assignee: Nippon Kayaku Kabushiki Kaisha, Tokyo, Japan

[21] Appl. No.: 450,832

[22] Filed: Dec. 14, 1989

[30] Foreign Application Priority Data

Dec. 27, 1988 [JP] Japan ................. 63-327843

[51] Int. Cl.$^5$ .................. C07C 57/60; C07C 69/618; C07C 69/003
[52] U.S. Cl. ........................ 560/43; 562/456
[58] Field of Search ................. 562/456; 560/43

[56] References Cited

U.S. PATENT DOCUMENTS 3,573,290  3/1971  Sallmann et al. ............ 562/456
3,801,636  4/1974  Horrom ..................... 562/456
3,860,639  1/1975  Schultz .................... 562/456

FOREIGN PATENT DOCUMENTS 837134    3/1970  Canada .................... 562/456
10003532  8/1979  European Pat. Off. .

OTHER PUBLICATIONS

The Journal of Organic Chemistry, vol. 43, No. 15, pp. 2941–2946.

Primary Examiner—J. E. Evans
Attorney, Agent, or Firm—Henry C. Nields

[57] ABSTRACT

A 2-acylamino-5-halogenated-cinnamic acid derivative represented by the formula (III) which is useful as an intermediate for producing medicines and agricultural chemicals:

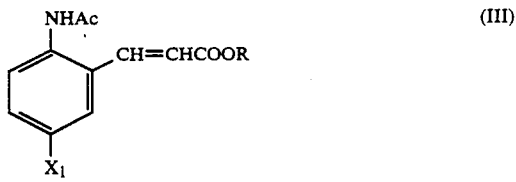

(III)

wherein Ac represents a lower acyl group, R represents a hydrogen atom or a lower alkyl group, and $X_1$ represents a halogen atom. This derivative is obtained by reacting a compound represented by the formula (I),

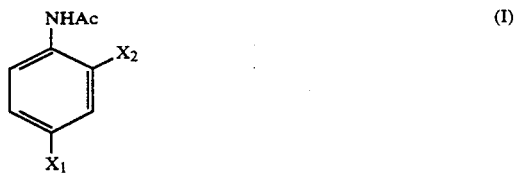

(I)

wherein Ac and $X_1$ are as defined above, and $X_2$ represents a bromine or iodine atom, with acrylic acid or its ester represented by the formula (II),

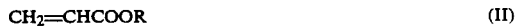

$CH_2=CHCOOR$   (II)

where R is as defined above, in the presence of a palladium catalyst, a tri(unsubstituted- or substituted-phenyl)phosphine and an acid-binding agent.

8 Claims, No Drawings

2-ACYLAMINO-5-HALOGENATED-CINNAMIC ACID DERIVATIVE AND METHOD FOR ITS PRODUCTION

BACKGROUND OF THE INVENTION

1. Field of the Invention

The present invention relates to a novel 2-acylamino-5-halogenated-cinnamic acid derivative and a method for its production.

2. Description of the Prior Art

Cinnamic acid derivatives are useful intermediates for producing medicines and agricultural chemicals, particularly indazoleacetic acids and indoleacetic acids. However, as to a 2-acylamino-5-halogenated-cinnamic acid derivative represented by the formula (III) shown later, neither its presence nor production is known. As a synthetic method for cinnamic acid derivatives having an amino group, for example a one for the following cinnamic acid derivative is known [J. Org. Chem., 43, 2945 (1978)]:

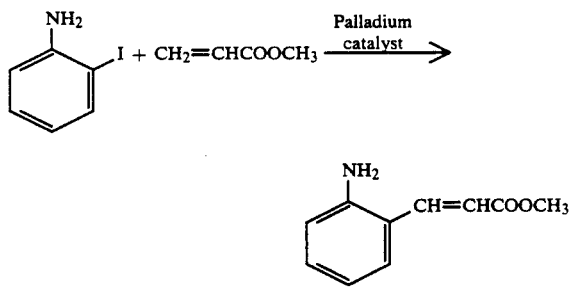

This method is industrially problematic in that it requires a reaction time as long as 80 hours and a large amount of the expensive catalyst. It is considered that such a long reaction time is caused by the coordination of the 2-amino group to the catalyst which lowers the activity of the catalyst.

Now, there is a demand for the development of cinnamic acid derivatives which are useful to synthesize an intermediate for medicines and agricultural chemicals, particularly 5-halogenated-indazoleacetic acids and 5-halogenated-indoleacetic acids, and a method for producing the same.

SUMMARY OF THE INVENTION

The present inventors have extensively studied to solve the foregoing subjects, and as a result have completed the present invention. The present invention provides a 2-acylamino-5-halogenated-cinnamic acid derivative represented by the formula (III),

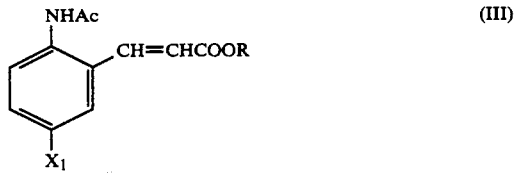

wherein Ac represents a lower acyl group, $X_1$ represents a halogen atom, and R represents a hydrogen atom or a lower alkyl group, and a method for producing said derivative represented by the formula (III) which comprises reacting a compound represented by the formula (I),

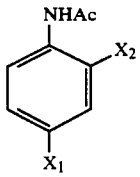

wherein Ac and $X_1$ are as defined above, and $X_2$ represents a bromine or iodine atom, with acrylic acid or its ester represented by the formula (II),

$$CH_2=CHCOOR \qquad (II)$$

wherein R is as defined above, in the presence of a palladium catalyst, a tri(unsubstituted- or substituted-phenyl)phosphine and an acid-binding agent.

Among the cinnamic acid derivatives represented by the formula (III), particularly useful ones are 2-acetylamino-5-chlorocinnamic acid, 2-acetylamino-5-fluorocinnamic acid, methyl 2-acetylamino-5-chlorocinnamate, ethyl 2-acetylamino-5-chlorocinnamate, methyl 2-propionylamino-5-fluorocinnamate, etc.

Examples of the substitution of iodobenzene or bromobenzene having an acylamino group at the 2-position by acrylic acid or acrylate have not been reported till now. It has been presumed that high yields cannot be expected from this reaction, because there are a fear of the steric hindrance caused by the acylamino group and a fear of the hydrolysis of the group. Contrary to this presumption, there are no such fears at all in the method of the present invention. The compound of the present invention represented by the formula (III) can easily be converted to 5-halogenated-indazole-3-acetic acids by partial reduction of the vinylene group (—CH=CH—), formation of an N-nitroso group and then dehydrative cyclization, or by hydrolysis of the ester group and acylamino group, diazotization of the resulting 5-halogenated-2-aminocinnamic acid and then reductive cyclization.

DESCRIPTION OF THE PREFERRED EMBODIMENTS

The present invention will be illustrated in more detail.

The compound represented by the formula (I), a starting compound, can easily be obtained by brominating or iodinating 4-halogenated-aniline and then acylating the resulting compound with the acid anhydride or acid chloride of a lower fatty acid such as acetic acid anhydride, butyric acid anhydride, acetyl chloride, propionyl chloride, etc. In the formula (I), $X_1$ is a chlorine, fluorine, iodine or bromine atom, among which a chlorine and fluorine atoms are preferred. Ac is a lower acyl group such as formyl, acetyl, propionyl, butyryl, valeryl, etc., among which acetyl is preferred.

The compound represented by the formula (II) includes acrylic acid, methyl acrylate, ethyl acrylate, butyl acrylate, octyl acrylate, etc. Its amount used is usually 1.0 to 3.0 moles based on 1 mole of the compound represented by the formula (I).

Examples of a palladium catalyst which can be used in the method of the present invention include palladium salts (e.g. palladium chloride, palladium acetate, palladium sulfate), palladium black and palladium adsorbed to an adsorbent (e.g. activated carbon, diatomaceous earth, etc.). The amount of the palladium catalyst used is usually 1/10 to 1/5000 mole, preferably 1/100 to 1/1000 mole based on 1 mole of the compound represented by the formula (I).

The amount of another catalyst, a tri(unsubstituted- or substituted-phenyl)phosphine, is 1 to 4 moles, particularly preferably 2 moles based on 1 mole of the palladium catalyst. Examples of a usable tri(unsubstituted- or substituted-phenyl)phosphine include triphenylphosphine and its derivatives having a substituent on the phenyl groups such as tri(p-tolyl)phosphine, tri(2,4-dimethylphenyl)phosphine, tri(2,4,6-trimethylphenyl)phosphine, tri(p-chlorophenyl)phosphine, etc.

Both inorganic bases and organic bases may be used as the acid-binding agent. Particularly, preferred bases are relatively weak inorganic bases such as potassium acetate, sodium acetate, ammonium acetate, calcium acetate, potassium hydrogencarbonate, sodium hydrogencarbonate, ammonium hydrogencarbonate, potassium carbonate, sodium carbonate, ammonium carbonate and calcium hydroxide, and organic bases such as trimethylamine, triethylamine, tributylamine, pyridine, piperidine, N-methylpiperidine and 4-diazabicyclo-[2,2,2]octane. The amount of the acid-binding agent is preferably 1 to 3 moles based on 1 mole of the compound represented by the formula (I).

Generally, solvents which may suitably be employed in this reaction are amides and alcohols, and the former solvents are particularly preferred. For example, these include N,N-dimethylformamide, N,N-dimethylacetamide, N-methylpyrrolidone, dimethylimidazolidinone (DMI), dimethyl sulfoxide, hexamethylphosphoramide, dioxane, ethylene glycol monomethyl ether, ethylene glycol monoethyl ether and methyl isobutyl ketone. Inactive solvents such as benzene, toluene, xylene and chlorobenzene may be used together with the foregoing solvents. The amount of the solvent used is usually 2 to 10 times by weight based on the total weight of the materials used.

The reaction temperature is preferably 50° to 250° C., more preferably 100° to 150° C. The reaction time is 1 to 8 hours, preferably 2 to 6 hours. After completion of the reaction, the desired compound can be isolated as crystal by pouring the reaction solution into water and separating the precipitated crystal, or by distilling the solvent out of the reaction solution The compound of the formula (III) obtained by the present invention is useful to synthesize 5-halogenated-indazoleacetic acids and 5-halogenated-indoleacetic acids which are useful as medicines and agricultural chemicals, particularly as a plant growth regulator.

The present invention will be illustrated more specifically with reference to the following examples, but it is not limited to these examples.

EXAMPLE 1

To a 200-ml flask were successively charged 40 ml of N,N-dimethylformamide (hereinafter abbreviated as DMF), 20 g (0.0677 mole) of 2-acetylamino-5-chloroiodobenzene, 5.94 g (0.069 mole) of methyl acrylate, 6.94 g (0.0846 mole) of anhydrous sodium acetate, 10 mg of palladium chloride and 30 mg of triphenylphosphine in this order. This mixture was stirred at 130° to 135° C. for 3 hours and poured into 200 ml of water, and then a large amount of crystal precipitated. This crystal was filtered off, thoroughly washed with water and dried in vacuo to obtain 14.1 g of methyl 2-acetylamino-5-chlorocinnamate. The yield was 82.2% of the theoretical value, and the melting point was 172° to 174° C. The nuclear magnetic resonance spectrum ($^1$H-NMR) and infrared absorption spectrum (IR) of this compound were as follows:

$^1$H-NMR ($\delta$, DMSO-d$_6$): 2.04 (s, —COCH$_3$), 7.69 (d, —CH=CHCOO—, 16 Hz), 3.68 (s, —OCH$_3$), 9.78 (bs, —NH), 6.48 (d, —CH=CH—COO—, 16 Hz)

IR (KBr method): 3250 cm$^{-1}$ ($\nu$NH), 1720 cm$^{-1}$ ($\nu$C=O, ester), 1660 cm$^{-1}$ ($\nu$C=O, amide), 1635 cm$^{-1}$ ($\nu$C=O, ester)

EXAMPLE 2

To a 200-ml flask were added 40 ml of DMF, 20 g (0.0677 mole) of 2-acetylamino-5-chloroiodobenzene, 5.85 g (0.0812 mole) of acrylic acid, 7.77 g (0.0947 mole) of anhydrous sodium acetate, 10 mg of palladium chloride and 30 mg of triphenylphosphine. This mixture was stirred at 115° C. for 5 hours and poured into 200 ml of water, and then a large amount of crystal precipitated. Sodium hydroxide was added to this aqueous solution containing the crystal while stirring the solution as it was, until the pH of the solution became 9.0. Then, the crystal dissolved in the solution to obtain a uniform solution. Thereafter, 2 g of activated carbon was added to the solution, and after stirring at room temperature for 15 minutes, the insoluble matter was filtered off. The filtrate was acidified to a pH of 1.5 with conc. hydrochloric acid, and then white crystal precipitated. This crystal was filtered off and vacuum-dried to obtain 13.9 g of 2-acetylamino-5-chlorocinnamic acid. The yield was 85.2% of the theoretical value, and the melting point was 243° to 245° C. The $^1$H-NMR and IR of this compound were as follows:

$^1$H-NMR ($\delta$, DMSO-d$_6$): 2.07 (s, —COCH$_3$), 9.83 (bs, —NH—), 6.51 (d, —CH=CHCOO—, 16 Hz), 7.68 (d, —CH=CHCOO—, 16 Hz)

IR (KBr method): 3250 cm$^{-1}$ ($\nu$NH), 1665 cm$^{-1}$ ($\nu$C=O, amide), 1625 cm$^{-1}$ ($\nu$C=O), 1700 cm$^{-1}$ ($\nu$C=O carboxylic acid)

EXAMPLE 3

Reaction was carried out in the same manner as in Example 1 except that 30 mg of tri-o-tolylphosphine was used in place of triphenylphosphine to obtain 14.5 g of methyl 2-acetylamino-5-chlorocinnamate. The yield was 84.2% of the theoretical value.

EXAMPLE 4

Procedure was carried out in the same manner as in Example 1 except that 4.5 g of sodium carbonate was used in place of anhydrous sodium acetate to obtain 12.8 g of methyl 2-acetylamino-5-chlorocinnamate. The yield was 75.0% of the theoretical value.

EXAMPLE 5

Procedure was carried out in the same manner as in Example 1 except that 7.45 g (0.0745 mole) of ethyl acrylate was used in place of methyl acrylate to obtain 16.3 g of ethyl 2-acetylamino-5-chlorocinnamate. The yield was 90.0% of the theoretical value, and the melting point was 157° to 159° C. The $^1$H-NMR and IR of this compound were as follows:

$^1$H-NMR ($\delta$, DMSO-d$_6$): 2.09 (s, —COCH$_3$), 1.26 (t, —CH$_2$CH$_3$, 7 Hz), 4.18 (q, —CH$_2$CH$_3$, 8 Hz), 9.87 (bs, —NH—), 6.62 (d, —CH=CHCOO—, 16 Hz), 7.78 (d, —CH=CHCOO—, 16 Hz)

IR (KBr method): 3260 cm$^{-1}$ ($\nu$NH), 1660 cm$^{-1}$ ($\nu$C=O, amide), 1640 cm$^{-1}$ ($\nu$C=O), 1720 cm$^{-1}$ ($\nu$C=O ester)

EXAMPLE 6

To 100 ml of ethylene glycol monoethyl ether were added 10 g of 2-acetylamino-5-chloroiodobenzene, 3.96 g of anhydrous potassium acetate, 2.84 g of methyl acrylate, 5.8 mg of palladium acetate and 17.4 mg of triphenylphosphine. The resulting mixture was allowed to react at 130° C. for 8 hours under the stream of a nitrogen gas. The reaction solution was cooled to 50° C. and poured into 300 ml of water, and then a large amount of white crystal precipitated. This crystal was filtered off, washed with water and vacuum-dried to obtain 6.2 g of methyl 2-acetylamino-5-chlorocinnamate. The yield was 72.5%.

EXAMPLE 7

To a 200-ml flask were added 40 ml of DMF, 20 g (0.0717 mole) of 2-acetylamino-5-fluoroiodobenzene, 5.85 g (0.0812 mole) of acrylic acid, 7.77 g (0.0947 mole) of anhydrous sodium acetate, 10 mg of palladium chloride and 30 mg of triphenylphosphine. This mixture was stirred at 125° to 130° C. for 3 hours and poured into 200 ml of water, and then a large amount of crystal precipitated. Sodium hydroxide was added to this aqueous solution containing the crystal while stirring the solution as it was, until the pH of the solution became 9.0 to obtain a uniform solution. Thereafter, 2 g of activated carbon was added to the solution, and after stirring at room temperature for 15 minutes, the insoluble matter was filtered off. The filtrate was acidified to a pH of 4.0 with conc. hydrochloric acid, and then white crystal precipitated. This crystal was filtered off and vacuum-dried to obtain 12.6 g of 2-acetylamino-5-fluorocinnamic acid. The yield was 78.5% of the theoretical value, and the melting point was 232° to 233° C. The $^1$H-NMR and IR of this compound were as follows:

$^1$H-NMR ($\delta$, DMSO-d$_6$): 2.05 (s, —COCH$_3$), 9.77 (bs, —NH—), 6.36 (d, —CH=CHCOO—, 16 Hz), 6.62 (d, —CH=CHCOO—, 16 Hz)

IR (KBr method): 3280 cm$^{-1}$ ($\nu$NH), 1700 cm$^{-1}$ ($\nu$C=O, carboxylic acid), 1660 cm$^{-1}$ ($\nu$C=O amide), 1630 cm$^{-1}$ ($\nu$C=O)

EXAMPLE 8

Reaction was carried out in the same manner as in Example 1 except that 16.8 g (0.0677 mole) of 2-acetylamino-5-chlorobromobenzene was used in place of 2-acetylamino-5-chloroiodobenzene to obtain 14.7 g of methyl 2-acetylamino-5-chlorocinnamate. The yield was 85.4% of the theoretical value.

EXAMPLE 9

To a 200-ml flask were added 40 ml of DMF, and then 20 g (0.0717 mole) of 2-acetylamino-5-fluoroiodobenzene, 7.9 g (0.0789 mole) of ethyl acrylate, 7.5 g (0.0896 mole) of anhydrous sodium acetate, 11 mg of palladium chloride and 33 mg of triphenylphosphine were added in this order. This mixture was stirred at 130°-135° C. for 3 hours and poured into 200 ml of water, and then a large amount of crystal precipitated. This crystal was filtered off, thoroughly washed with water and vacuum-dried to obtain 14.1 g of ethyl 2-acetylamino-5-fluorocinnamte. The yield was 78.5% of the theoretical value. The purified product obtained by recrystallization from ethyl alcohol had the following physical properties:

Melting point: 143.5°-144.5° C.

$^1$H-NMR ($\delta$, DMSO-d$_6$): 2.05 (s, —COCH$_3$), 1.25 (t, —CH$_2$CH$_3$, 7 Hz), 4.17 (q, —CH$_2$CH$_3$, 7 Hz), 9.75 (bs, —NH—), 6.45 (d, —CH=CH—COO—, 16 Hz), 6.72 (d, —CH=CH—COO—, 16 Hz)

IR (KBr method): 3250 cm$^{-1}$ ($\nu$NH), 1660 cm$^{-1}$ ($\nu$C=O, amide), 1640 cm$^{-1}$ ($\nu$C=C), 1720 cm$^{-1}$ ($\nu$C=O, ester)

EXAMPLE 10

Procedure was carried out in the same manner as in Example 2 except that 21.9 g (0.0677 mole) of 2-butyrylamino-5-chloroiodobenzene was used in place of 2-acetylamino-5-chloroiodobenzene in Example 2 to obtain 13.6 g of 2-butyrylamino-5-chlorocinnamic acid. The yield was 75.0% of the theoretical value. The resulting product had the following physical properties:

Melting point: 248° C. (dec.)

$^1$H-NMR ($\delta$, DMSO-d$_6$): 2.28 (t, —CH$_2$CH$_2$CH$_3$), 0.91 (t, —CH$_2$CH$_2$CH$_3$), 1.30–1.80 (m-CH$_2$CH$_2$CH$_3$), 6.34 (d, —CH=CHCOO—), 6.62 (d, —CH=CHCOO—), 9.74 (bs, —NH—)

IR (KBr method: 3270 cm$^{-1}$ ($\nu$NH), 1658 cm$^{-1}$ ($\nu$C=O, amide), 1630 cm$^{-1}$ ($\nu$C=C), 1702 cm$^{-1}$ ($\nu$C=O, ester)

What is claimed is:

1. A 2-acylamino-5-halogenated-cinnamic acid derivative represented by the formula (III),

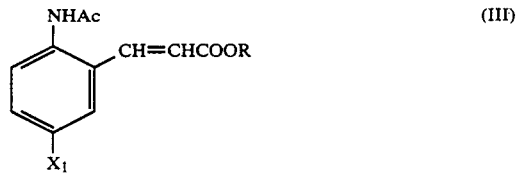

(III)

wherein Ac represents a lower acyl group, R represents a hydrogen atom or a lower alkyl group, and X$_1$ represents a halogen atom.

2. A 2-acylamino-5 halogenated-cinnamic acid derivative according to claim 1, wherein X$_1$ is a chlorine or fluorine atom.

3. A 2-acylamino-5-halogenated-cinnamic acid derivative according to claim 1, wherein Ac is a formyl, acetyl, propionyl, butyryl or valeryl group.

4. 2-Acetylamino-5-chlorocinnamic acid.
5. 2-Acetylamino-5-fluorocinnamic acid.
6. Methyl 2-acetylamino-5-chlorocinnamate.
7. Ethyl 2-acetylamino-5-chlorocinnamate.
8. Methyl 2-propionylamino-5-fluorocinnamate.

* * * * *